(12) United States Patent
Naidu et al.

(10) Patent No.: US 6,721,387 B1
(45) Date of Patent: Apr. 13, 2004

(54) METHOD OF AND SYSTEM FOR REDUCING METAL ARTIFACTS IN IMAGES GENERATED BY X-RAY SCANNING DEVICES

(75) Inventors: Ram Naidu, Brookline, MA (US); Ibrahim Bechwati, Roslindale, MA (US); Seemee S. Karimi, Malden, MA (US); Sergey Simanovsky, Brookline, MA (US); Carl R. Crawford, Brookline, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 10/171,116

(22) Filed: Jun. 13, 2002

Related U.S. Application Data (60) Provisional application No. 60/297,893, filed on Jun. 13, 2001.

(51) Int. Cl.[7] .................................................. A61B 6/03
(52) U.S. Cl. .............................................. 378/8; 378/4
(58) Field of Search .......................... 378/4, 8, 15, 901

(56) References Cited

U.S. PATENT DOCUMENTS

| | | | |
|---|---|---|---|
| 4,709,333 A | 11/1987 | Crawford | |
| 5,909,476 A | * 6/1999 | Cheng et al. | 378/4 |
| 5,933,471 A | * 8/1999 | Kalvin | 378/4 |
| 5,949,842 A | 9/1999 | Schafer et al. | 378/4 |
| 5,970,113 A | 10/1999 | Crawford et al. | 378/19 |
| 6,026,171 A | 2/2000 | Hiraoglu et al. | 382/100 |
| 6,067,366 A | 5/2000 | Simanovsky et al. | 382/100 |
| 6,111,974 A | 8/2000 | Hiraoglu et al. | 382/100 |
| 6,125,193 A | 9/2000 | Han | 382/131 |
| 6,317,509 B1 | 11/2001 | Simanovsky et al. | 382/131 |
| 2003/0147489 A1 | * 8/2003 | Bijjani et al. | 378/4 |

OTHER PUBLICATIONS

Crawford et al., "High Speed Reprojection And Its Applications", SPIE, vol. 914, Medical Imaging II (1988), pp. 311–319.

* cited by examiner

*Primary Examiner*—David V. Bruce
(74) *Attorney, Agent, or Firm*—McDermott, Will & Emery (57) ABSTRACT

A method of reducing metal artifacts in a computed tomography (CT) system includes:

A. generating a preliminary image from input projection data collected by the CT system;

B. identifying metal objects in the preliminary image;

C. generating secondary projections from the input projection data by removing projections of objects having characteristics that may cause the objects to be altered in a final artifact-corrected image.

D. extracting the projections of metal objects identified in step B from the secondary projection data generated in step C.

E. generating corrected projections by removing the projections of the metal objects extracted in Step D from the input projection data.

F. generating a final image by reconstructing the corrected projections generated in step E and inserting the metal objects identified in Step B into the final image.

33 Claims, 5 Drawing Sheets

METHOD OF AND SYSTEM FOR REDUCING METAL ARTIFACTS IN IMAGES GENERATED BY X-RAY SCANNING DEVICES

REFERENCE TO RELATED APPLICATIONS

This application claims the benefit of U.S. Provisional Patent Application Serial No. 60/297,893, filed Jun. 13, 2001, entitled METAL ARTIFACT REDUCTION FOR EXPLOSIVE DETECTION SYSTEMS, which application is hereby incorporated by reference in its entirety.

FIELD OF THE INVENTION

The present invention relates generally to a method of and system for reducing metal artifacts in images generated by x-ray scanning devices, and more particularly to a method of and system for manipulating an image generated by the x-ray CT scanner to remove metal artifacts.

BACKGROUND OF THE INVENTION

Computed Tomography (CT) inspection systems are utilized in many applications, including the fields of security and medicine. In the case of the security field, CT systems are used for scanning packages and baggage for the presence of explosives, weapons, and other contraband. While CT systems are very effective in detecting these types of objects, metal objects that may be present in the scanned items tend to generate streaks or artifacts in the resulting image, which degrade the quality of the image, causing the possibility of misread images. These artifacts appear in the form of dark and bright streaks that emanate from metal objects in the scanned item. These artifacts are caused because the metals objects greatly attenuate the x-ray beam and reduce the number of photons reaching the detector of the CT system, causing a low photon count at the detector. This results in a poor signal-to-noise ratio which causes high-frequency streak artifacts. Additionally, metal objects harden the x-ray beam by attenuating x-rays in an energy-specific manner. The resulting nonlinear changes in the projection data appear as low-frequency tail artifacts around the metal objects, as well as between the metal and other high-density objects.

Metal artifacts are problematic because they interfere with CT image analysis programs that are designed to identify features in the resulting image of the scanned item. For example, in programs that are designed to identify thin sheet objects which may be explosives, metal artifacts can cause the sheet object to appear distorted and possibly escape detection.

Prior art attempts at reducing metal artifacts in a CT image include removing the data associated with the metal objects from the scanned images, correcting the images by removing or reducing the metal artifacts and replacing the metal object data in the resulting images. However, in such systems, the integrity of any thin or sheet objects can be degraded, thus reducing the effectiveness of the detection system.

SUMMARY OF THE INVENTION

The present invention is directed to a method for correcting CT images for metal artifacts while preserving the integrity of thin objects in the images.

According to one aspect of the invention, a method of reducing metal artifacts in a computed tomography (CT) system includes:

A. generating a preliminary image from input projection data collected by the CT system;

B. identifying metal objects in the preliminary image;

C. generating secondary projections from the input projection data by removing projections of objects having characteristics that may cause the objects to be altered in a final artifact-corrected image.

D. extracting the projections of metal objects identified in step B from the secondary projection data generated in step C.

E. generating corrected projections by removing the projections of the metal objects extracted in Step D from the input projection data.

F. generating a final image by reconstructing the corrected projections generated in step E and inserting the metal objects identified in Step B into the final image.

Step B may include identifying objects in the preliminary image having intensities which are greater than a predetermined amount. Step B may further include selecting metal objects which generate artifacts. Step C may include identifying objects in the preliminary image having characteristics that may cause the objects to be altered in a final artifact-corrected image. Step C may further include generating a modified image by setting pixels in the preliminary image, which are not included in the objects identified in step C to a calculated value. The calculated value may be equal to mean value of the preliminary image determined using pixels other than the pixels included in the objects identified in step B. Step C may further include reprojecting the modified image and subtracting the reprojections from the input projection data to generate secondary projections which contain the input projection data with the projections of objects identified in step C removed. Step D may include identifying at least one region in the secondary projections which contain the projections of metal objects identified in step B. Step D may further include determining a baseline value of each of the at least one regions. The baseline value of each of the at least one region may be determined by linear interpolation between projection data surrounding the at least one region. Step D may further include subtracting each baseline value from the secondary projection values in its respective region to generate projection data corresponding to the metal projections in each region. The objects identified in step C may include objects in the preliminary image having at least one dimension which is less than a predetermined length. The objects identified in step C may include objects in the preliminary image having an intensity which differs from the mean intensity of the preliminary image by more than a predetermined threshold.

According to another aspect of the invention, a method of reducing metal artifacts in a computed tomography (CT) system includes:

A. generating a preliminary image from input projection data collected by the CT system;

B. identifying metal objects in the preliminary image which have generated metal artifacts in the preliminary image;

C. identifying objects in the preliminary image having characteristics which may cause the objects to be altered in a final artifact-corrected image;

D. generating a modified image by setting pixels in the preliminary image which are not included in objects identified in step C to a mean value of the preliminary image;

E. reprojecting the modified image;

F. subtracting the reprojections from the input projection data to generate secondary projections containing the preliminary image with the objects identified in step C removed;

G. identifying at least one region in the secondary image which contains projections of metal objects identified in step B;

H. determining a baseline value of each of the at least one regions;

I. subtracting each baseline value from the secondary projection values in its respective region to generate projection data corresponding to the metal object in each region;

J. subtracting the metal projection data from the input projection data to generate corrected projections;

K. reconstructing the final artifact-corrected image by:
  a. reconstructing corrected projections; and
  b. superimposing the metal objects identified in step B into the corrected image.

The objects identified in step C may include objects in the preliminary image having at least one dimension, which is less than a predetermined length. The objects identified in step C may include objects in the preliminary image having an intensity, which differs from a mean intensity of the preliminary image by more than a predetermined amount. In step G, the baseline value of each of the at least one region may be determined by linear interpolation between projection values surrounding the at least one region.

According to yet another embodiment of the invention, a system for reducing metal artifacts in a computed tomography (CT) system includes a tunnel having a platform disposed therein for receiving an object to be scanned, an x-ray source for directing x-rays at the object to be scanned, a detector array including a plurality of detectors for receiving the x-rays within the tunnel and processing means for reducing metal artifacts in images of the object reconstructed from the x-rays detected by the detectors. The processing means performs the steps of:

A. generating a preliminary image from input projection data collected by the CT system;

B. identifying metal objects in the preliminary image;

C. generating secondary projections from the input projection data by removing projections of objects having characteristics that may cause the objects to be altered in a final artifact-corrected image.

D. extracting the projections of metal objects identified in step B from the secondary projection data generated in step C.

E. generating corrected projections by removing the projections of the metal objects extracted in Step D from the input projection data.

F. generating a final image by reconstructing the corrected projections generated in step E and inserting the metal objects identified in Step B into the final image.

BRIEF DESCRIPTION OF THE DRAWINGS

The foregoing and other objects of this invention, the various features thereof, as well as the invention itself may be more fully understood from the following description when read together with the accompanying drawings in which.

DETAILED DESCRIPTION

The present invention is preferably directed to an x-ray CT scanner system, which is used to scan bags and packages in airports and other secure locations where the detection of contraband is essential. This invention is related to the systems disclosed in commonly-assigned U.S. Pat. Nos. 5,949,842 and 5,970,113, which are incorporated herein by reference. It will be understood, however, that the present invention may also be utilized to reduce metal artifacts in CT scanners used in the medical field and in any scanning system in which the reduction of artifacts is critical to the proper reconstruction of the scanned objects. For clarity and simplicity, definitions of the variables discussed in this application and the equations used throughout this application are listed in the Appendix of this application.

Figure 1:
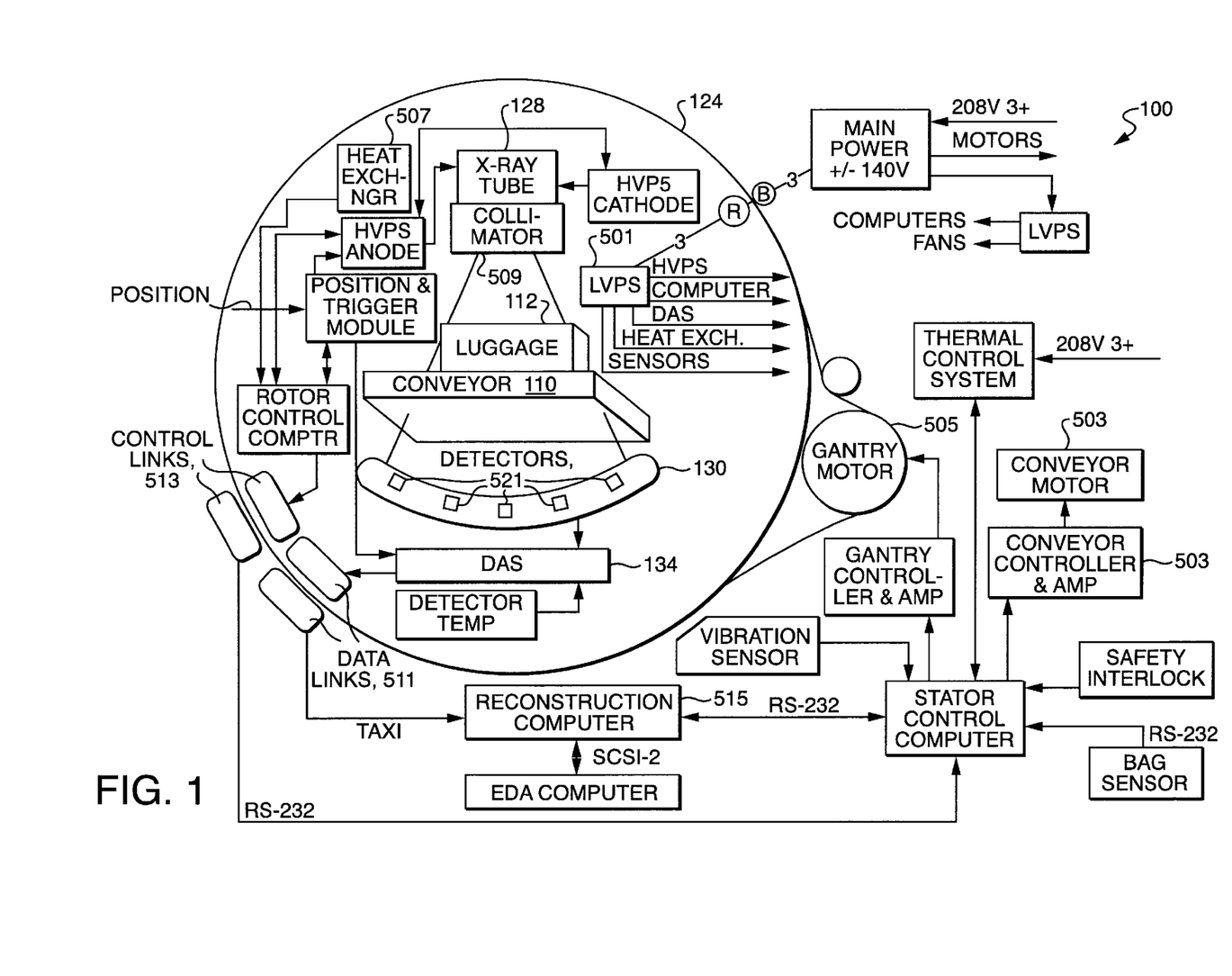
FIG. 1 is a schematic block diagram of a CT scanner in accordance with the present invention.

FIG. 1 is a mechanical/electrical block diagram of one embodiment of a baggage scanning system 100 of the invention. The mechanical gantry of the scanner 100 includes two major components, the disk 124 and the frame (not shown). The disk 124 is the rotational element which carries an X-ray assembly, a detector assembly 130, a data acquisition system (DAS) 134, a high-voltage power supply and portions of the monitor/control assembly, a power supply assembly and a data link assembly. The frame supports the entire system 100, including the baggage handling conveyor system 110. The disk 124 is mechanically connected to the frame via a duplex angular contact ball bearing cartridge. The disk 124 can be rotated at a constant rate by a belt, which can be driven by a DC servomotor 505. The gantry also contains X-ray shielding on the disk and frame assemblies.

In one embodiment, the baggage conveyor system 110 includes a single belt driven at a constant rate to meet specified throughput requirements, which, in one embodiment, include a requirement that 675 bags per hour be processed. The belt can be driven by a high-torque, low-speed assembly to provide a constant speed under changing load conditions. A low-attenuation carbon graphite epoxy material can be used for the portion of the conveyor bed in the X-ray. The total length of the conveyor is designed to accommodate three average length bags. A tunnel is used around the conveyor to meet the appropriate safety requirement of a cabinet X-ray system.

In one embodiment, input power of 208 volts, 3-phase, 30 amps services as the main supply which can provide power for the entire system. This input power can be supplied by the location at which the system is installed. Power is transferred from the frame through a series of frame brushes which make continuous contact with the metal rings mounted to the disk 124. The low-voltage power supply 501 on the disk 124 provides power for the DAS 134, the X-ray cooling system and the various monitor/control computers and electronics. A low-voltage power supply on the frame provides power for the reconstruction computer and the various monitor/control electronics. The conveyor motor 503, the gantry motor 505, the high-voltage power supply and the X-ray coolant pump can all be supplied power directly from the main supply.

The high-voltage power supply provides power to the X-ray tube 128. The supply can provide a dual voltage across the cathode/anode which can be modulated at 540 Hz.

The driving waveform can be in the form of a sine wave. This supply can also provide X-ray filament power. The supply current can be held approximately constant for both voltages.

The X-ray assembly includes a bipolar, fixed-anode X-ray tube 128, a heat exchanging system 507, a collimator 509, shielding, an X-ray sensor and an alignment/mounting plate. The collimator can provide an X-ray cone beam of 61° fan angle by 6° spread. The heat exchanging system 507 includes a pump, radiator, fan and plumbing. The heat transfer liquid can be a high-dielectric oil. An alignment plate can be used for mounting the tube 128 to the disk 124 to reduce the field replacement complexity and time. An X-ray sensor can be included to provide X-ray intensity feedback.

Figure 2:
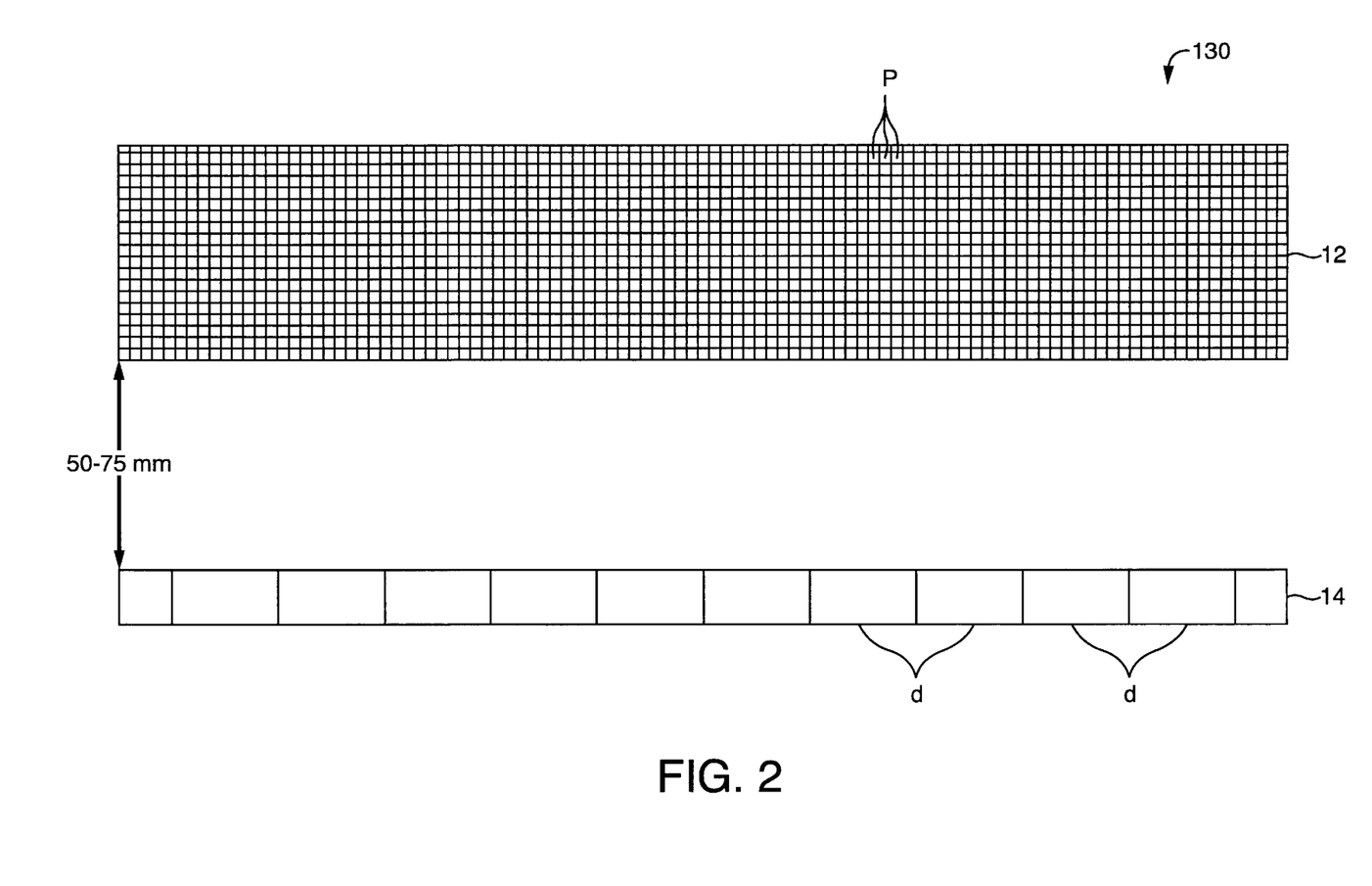
FIG. 2 is a schematic diagram of the detector array of the scanner of FIG. 1 in accordance with the present invention.

The dual-energy X-rays strike the baggage, and some portion of the X-rays pass through and strike the detector assembly 130. Detector assembly 130 is schematically shown in FIG. 2 and includes a primary array 12 of detectors and a row 14 of scatter detectors. For the purposes of this description, the detectors in the primary array 12 are generically referred to with the index "p" and detector in the scatter row 14 are generically referred to with the index "d". While not shown to scale in the figure, the array 12 can have 16 or more rows of detectors with approximately 1,000 detectors in each row. Scatter detector row 14 need only include approximately 20–40 detectors in the preferred embodiment, in order to reduce the overall cost of the system. Furthermore, any type and/or size of scatter detector may be utilized in the scatter detector row 14. Preferably, the scatter row 14 is spaced approximately 50–75 mm from the array 12. Preferably, the x-ray beam is collimated to cover a narrow path of the detectors in array 12 and the scatter detector row 14 is located outside of the penumbra of the X-ray beam to insure that the scatter detectors detect only scatter and not the main x-ray beam.

The detector assembly 130 can be made up of scintillators, photodiodes, mounting substrates and a mechanical mounting spine. A spine heater with temperature sensors 521 can also be included. The detector assembly 130 performs an analog conversion from X-ray to visible photons and then to electrical current. The scintillators are made from cadmium tungstate crystal which is thick enough to almost completely absorb all of the X-rays. The scintillators convert the X-rays into visible photons. The crystal can be surrounded on all sides except the bottom by optically reflective material. Thus, the visible photons can pass out of the bottom of the crystal. The photodiodes can be connected to the bottom of the crystal by means of an optically transmissive adhesive. The photodiodes emit a current which decreases logarithmically with the bag's X-ray attenuation. The photodiodes can be attached to a ceramic substrate which can be sized to fit several detectors.

This electrical substrate can be wire bonded and epoxied to a flexprint which contains a connector which mounts to the DAS 134. Each detector substrate can then be mechanically attached to a mounting spine that has the fan beam radius and projects in the Z-direction. This spine can then be rigidly secured to the disk 124.

The DAS 134 can sample the detector currents, multiplex the amplified voltages to a set of 16-bit analog-to-digital converters and multiplex the digital outputs to the non-contact serial data link 511. The DAS 134 can be triggered by the angular position of the disk 124.

The non-contact links 511 and 513 transfer the high-speed digital DAS data to the image reconstruction processor 515 and low-speed monitor/control signals back and forth between the disk and frame control computers. The data link 511 can be based upon an RF transmitter and receiver. The transfer protocol can be TAXI™ which is capable of up to 350 Mbits/sec. The control link 513 can be based on wireless LAN technology, which can include identical PCMCIA cards mounted in both the frame and disk computers. The cards can have both a transmitter and receiver electronics and can emulate a standard Ethernet card. A point-to-point network is therefore established for the low-speed monitor and control communication.

The image reconstructor converts the digital line integrals from the DAS 134 into a set of two-dimensional images of bag slices for both the high and low energies. The CT reconstruction can be performed via a helical-cone beam solution. The reconstructor can include embedded software, a high-speed DAS port, an array processor, a DSP-based convolver, an ASIC-based backprojector, image memory, UART control port, and a SCSI output port for image data. The array processor can perform data corrections and interpolation. The reconstructor can be self-hosted and can tag images based upon the baggage information received over the UART interface to the frame computer.

The monitor and control system can be a PC-based embedded control system. All subsystems can be monitored for key health and status information. This system can also control both motion systems, can sense baggage information, can control the environment, e.g., temperature, humidity, etc., can sense angular position of the disk 124 and can trigger the DAS and HVPS. This system can also have a video and keyboard interface for engineering diagnostics and control Additionally, a control panel can be included for field service.

Figure 3:
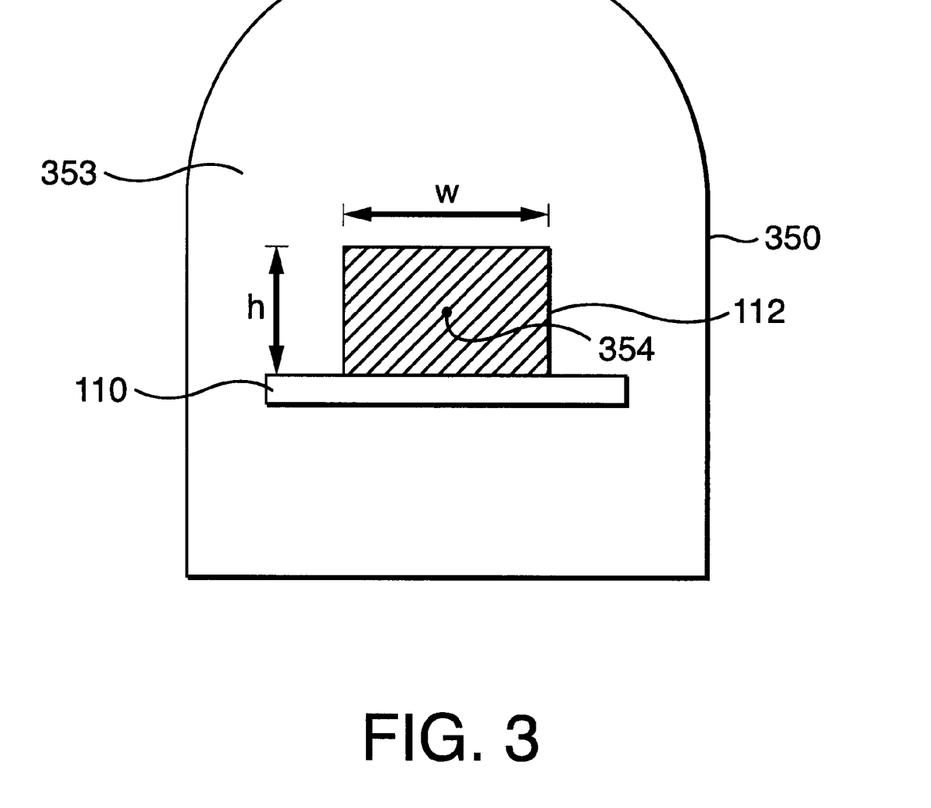
FIG. 3 is a schematic diagram of the field-of-view of the CT scanner of FIG. 1.

FIG. 3 is a schematic pictorial diagram of the field of view of the scanner, used to illustrate the adaptive reconstruction window of the invention. The field of view is shown to include the tunnel 350 and conveyor 110 on which is located a bag 112 having a height h and a width w.

Generally, the present invention reduces metal artifacts in CT images while preserving the integrity of thin objects in the images. For the sake of this description, the term "rubout region" is defined for each view as the set of projection samples which correspond to line integrals through artifact-producing metal objects within the item being scanned by the CT system. The rubout region contains the sum of projections of the metal object with the projections of non-metallic objects within the scanned item. The term "baseline" is defined as the sum of the projections of the non-metallic objects. This method of the present invention includes the following generalized steps:

1. Identification of metal objects.
    (a) A preliminary image is reconstructed from input projection data generated by the CT system.
    (b) Metal objects which create metal artifacts in the preliminary image are identified and selected.
2. Reprojection of high-contrast objects and thin sheet objects.
    (a) Objects having a sheet-like appearance are identified in the preliminary image.
    (b) High-contrast objects, excluding the metal objects selected in step 1(b), are identified in the preliminary image.
    (c) The pixels in the preliminary image, excluding the pixels selected in step 2(a) and 2(b), are set to the mean of the preliminary image to create a modified image.

(d) The modified image is reprojected.
(e) The reprojections are subtracted from the input projections to yield modified input projections.
3. Removal of metal object projections.
  (a) Rubout regions containing the projections of the metal objects selected in Step 1(b) are determined in the modified input projections.
  (b) The baseline under each rubout regions is determined by linear interpolation.
  (c) The baseline is subtracted from the rubout regions to yield the metal projections.
  (d) The metal projections are subtracted from the input projections to yield corrected projections.
4. Reconstruction of the final, corrected image.
  (a) The corrected projections are reconstructed.
  (b) The pixels included in the metal objects selected in step 1(b) are superimposed on the reconstructed image to yield the final corrected image.

Each of these steps is described in detail below.

Figure 4:
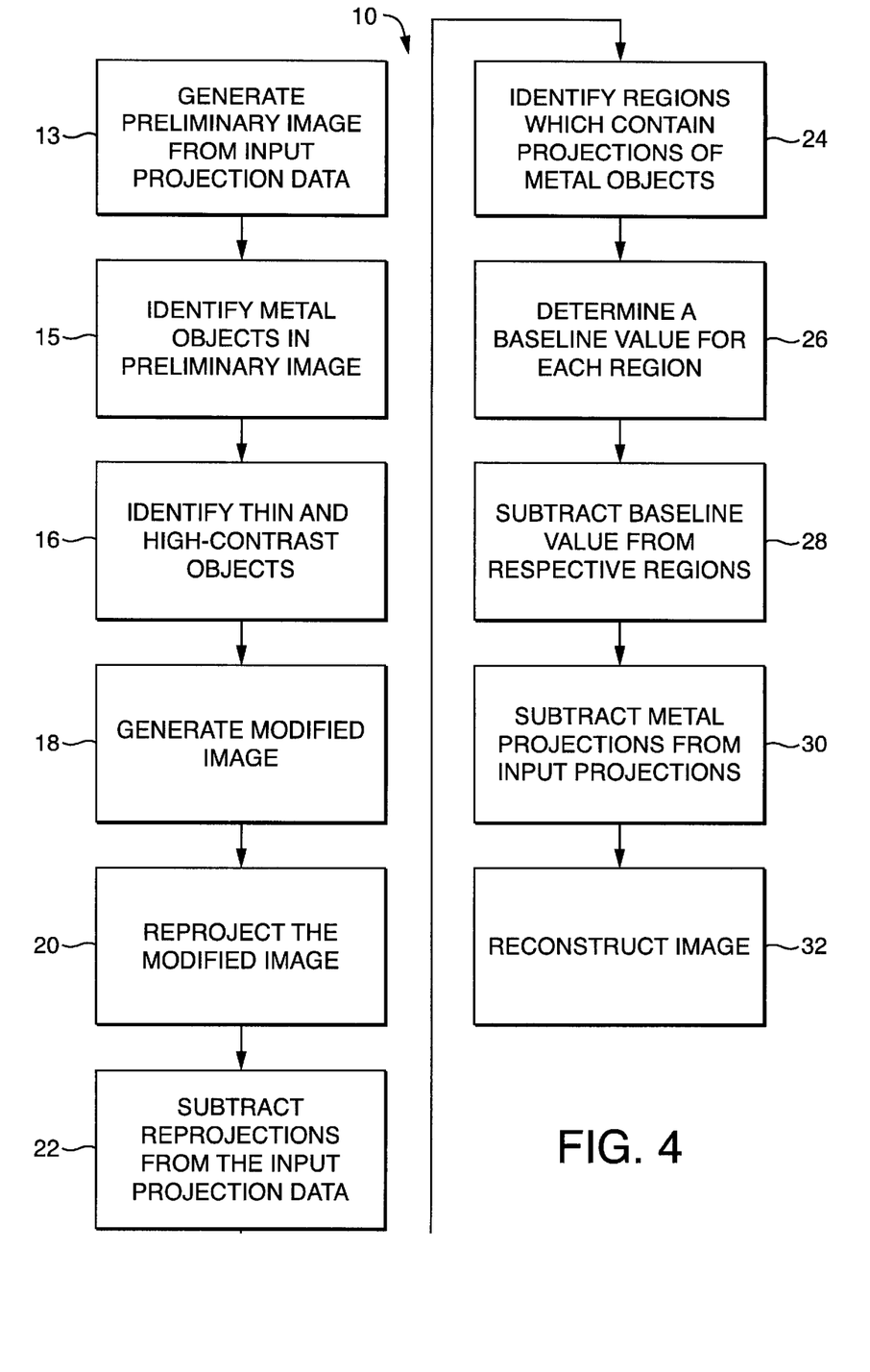
FIG. 4 is a flow diagram of the method of the present invention.
Figure 5A:
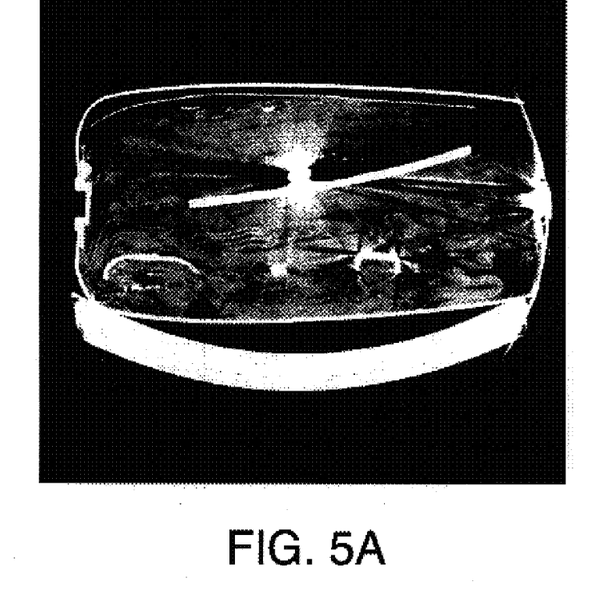
FIG. 5A is a CT scanner image of an item prior to the application of the present invention.

Referring now to FIG. 4, which is a flow diagram 10 showing the steps involved in the method of the present invention, the invention will be described in greater detail. In step 13, a preliminary image is reconstructed from input projection data generated by the CT system. The preliminary image is reconstructed using filtered backprojection, as is currently standard in the relevant art. An example image is shown in FIG. 5A, which is an image of a suitcase 40 reconstructed from input projection data generated by the CT scanning system. Shown in the image of FIG. 5A are a sheet explosive 42, a metal object 44 and metal artifacts 46 generated by the metal object 44. The purpose of the present invention is to reduce or eliminate the artifacts 46 while maintaining the integrity of the sheet 42 in the image. Step 13 enables the determination of the location of artifact-producing metal objects within the field of view of the CT scanner.

In step 15, FIG. 4, metal objects in the preliminary image are identified based on the intensity value of pixels in the preliminary image. Pixels of the image having an intensity greater than, for example, 2,000 HU are identified as belonging to a metal object in the image. The metal objects are selected based on their intensity in the preliminary image either manually by an operator of the system or automatically and a rectangular Region of Interest (ROI) is drawn around the metal object.

The dimensions of the ROI are used to determine the semi-major and semi-minor axes (a, b) of an ellipse that is inscribed within the ROI. The pixel coordinates $(i_c, j_c)$ of the center of the ROI and the axes of the ellipse are determined and written to a text file in memory. This text file is utilized in subsequent steps of the invention.

In the next steps, thin, sheet objects and high-contrast objects are identified, step 16, and a modified image including the sheet objects and high-contrast objects is generated from the preliminary image, step 18. Pixels in the modified image which are not included in the sheet objects and high-contrast objects are replaced by the mean value of the preliminary image.

In step 16, sheet objects are identified in the preliminary image according to the method disclosed in commonly-assigned U.S. Pat. Nos. 6,067,366; 6,111,974; and 6,317,509, which patents are hereby incorporated into this application in their entireties. This method, called the "CFAR algorithm", statistically determines whether a pixel in the image belongs to a sheet image. Pixels detected by the CFAR algorithm are connected and labeled using a standard connected component labeling algorithm. The labeled objects are then discriminated by their density. If the density is greater than a predetermined threshold, the object is determined to be a sheet object. An image $I_s$ is generated which includes pixels that are included in the sheet objects. All other pixels in the image are set to zero intensity.

Step 16 also includes the identification of high-contrast objects in the preliminary image. High-contrast objects are defined as those objects for which the pixel intensity differs from the mean intensity of the preliminary image, $\mu_i$, by more than a predetermined threshold. In other words, the pixels are selected as high-contrast if they have an intensity greater than or equal to $\mu_i+T_{hcmax}$ or an intensity less than or equal to $\mu_i-T_{hcmin}$. These objects include bright metal objects that were not selected for correction as well as dark objects in the image. The high contrast pixels, which do not belong to the selected metal objects, are then added to the image $I_s$ to form the modified image $I_{shc}$, step 18. The modified image $I_{shc}$ is formed according to the following:

$$I_{shc}(i,j) = \begin{cases} I_s(i,j) & \text{if } I_s(i,j) \neq 0 \\ I_i(i,j) & \text{if } I_i(i,j) \geq \mu_i + T_{hcmax} \text{ and } (i,j) \notin metalROI \\ I_i(i,j) & \text{if } I_i(i,j) \leq \mu_i - T_{hcmin} \text{ and } (i,j) \notin metalROI \\ \mu_i & \text{otherwise} \end{cases} \quad (1)$$

where $I_i$ is the preliminary image; and (i,j) represent the x and y coordinates of a pixel in each image.

In step 20, the modified image $I_{shc}$ is reprojected to obtain reprojections $R_\theta(t)$. The reprojections are performed along parallel rays as described in an article co-authored by one of the inventors or the present invention entitled "High Speed Reprojection and Its Applications", SPIE vol. 914 Medical Imaging II (1988) 311–318, which article is hereby incorporated by reference in its entirety. The reprojections are interpolated so that the number of samples and views in the reprojections are equal to the number of samples and views in the input projections.

In step 22, the reprojections $R_\theta(t)$ are subtracted from the input projections $P_\theta(t)$ to remove the sheet objects and high-contrast objects from the input projections. The resulting secondary projections $Q_\theta(t)$ contain the projections of low-contrast objects and the selected metal objects, but exclude the projections of sheet objects and high contrast objects other than the selected metal objects.

In step 24, the rubout regions in $Q_\theta(t)$, which correspond to projections through the selected metal objects, are determined. The rubout regions are determined based on the location of the selected metal objects in the preliminary image and the scanner geometry. For example, in a single ROI, the rubout region for each view is defined as the set of detectors, which lies within the projection of the ellipse inscribed within the ROI. If $t_{ro}(\theta)$ represents the rubout region for the ROI in view $\theta$:

$$t \in t_{ro}(\theta) \text{ if } |t-t_c| \leq \sqrt{a_x^2\cos^2\theta + b_y^2\sin^2\theta}. \quad (2)$$

If, for a given view, rubout regions are within a predetermined distance of each other, they are combined into a single rubout region. Rubout regions are determined for all ROIs. The process for determining rubout regions is described in greater detail in U.S. Pat. No. 4,709,333 (hereinafter the '333 patent), which patent is incorporated by reference in its entirety into the present application.

In step 26, the baseline for the data in each rubout region is determined using linear interpolation of data from valid detector readings on either side of the rubout regions. This process is also disclosed in the '333 patent. If $t_s$ and $t_e$ represent the first and last detectors in the rubout region of interest for view $\theta$, $$t_s(\theta)=t_c-\lfloor\sqrt{a_x^2\cos^2\theta+b_y^2\sin^2\theta}\rfloor; \text{ and} \qquad (3)$$

$$t_e(\theta)=t_c+\lceil\sqrt{a_x^2\cos^2\theta+b_y^2\sin^2\theta}\rceil. \qquad (4)$$

The baseline is determined as:

$$B_\theta(t)=Q_\theta(t_s-1)+m_\theta(t_s,t_e)[Q_\theta(t)-Q_\theta(t_s-1)] \, t\epsilon t_{ro}(\theta) \qquad (5)$$

where $$m_\theta(t_s, t_e) = \frac{Q_\theta(t_e+1) - Q_\theta(t_s-1)}{t_e - t_s + 2}. \qquad (6)$$

The baseline is calculated on a view-by-view basis.

In step 28, the baseline $B_\theta(t)$ determined in step 26 is subtracted from the secondary projections $Q_\theta(t)$ in order to obtain the projections of the metal object projections $M_\theta(t)$:

$$M_\theta(t)=Q_\theta(t)-B_\theta(t), \, t\epsilon t_{ro}(\theta) \qquad (7)$$

In step 30, the metal object projections $M_\theta(t)$ are subtracted from the input projections $P_\theta(t)$ to remove the metal object projections from the input projections, thereby generating the corrected projections $F_\theta(t)$. The corrected projections contain all of the projection data from the input projections, but exclude the signature of the metal objects.

Finally, in step 32, the corrected projections $F_\theta(t)$ are reconstructed using filtered backprojection to generate the final corrected image $I_c$ having reduced metal artifacts. Pixels corresponding to metal objects selected for correction are superimposed on the corrected image as described in U.S. Pat. No. 6,125,193, which patent is incorporated by reference in its entirety into the present application. For example, for each ROI, if the pixels within the ROI are greater than or equal to a threshold $T_m$, the pixels are superimposed on the corrected image to generate the corrected image $I_{cm}$ according to the following:

$$I_{cm}(i, j) = \begin{cases} I_i(i, j) & \text{if } I_i(i, j) \geq T_m \text{ and } \left(\frac{i-i_c}{a}\right)^2 + \left(\frac{j-j_c}{b}\right)^2 \leq 1 \\ I_c(i, j) & \text{otherwise} \end{cases} \qquad (8)$$

Figure 5B:
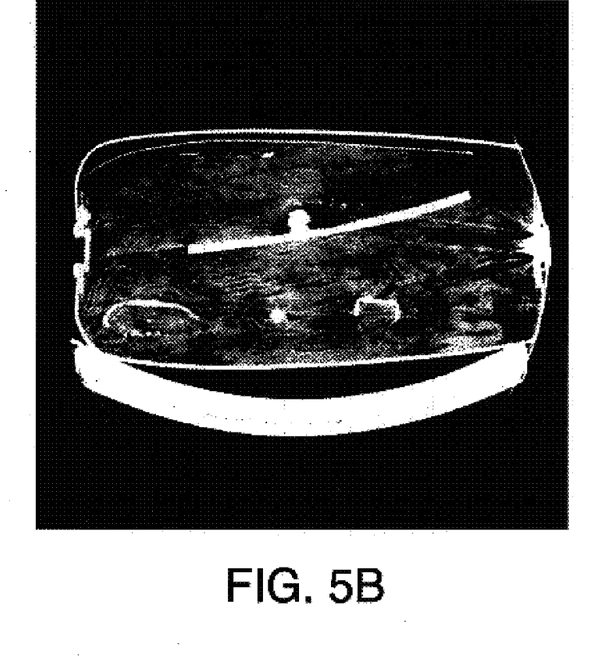
FIG. 5B is a CT scanner image of an item after to the application of the present invention.

FIG. 5B is the final corrected image $I_{cm}$ of the preliminary image shown in FIG. 5A. As can be seen in FIG. 5B, the metal artifacts 46 generated by metal object 44 are greatly reduced, while the sheet object 42 remains intact. This enables security personnel to more accurately inspect the contents of scanned items.

While the invention has been described in connection with security scanning systems for inspecting luggage, packages, etc., it will be understood that the invention may be utilized in connection with medical scanners to reduce artifacts caused by metal clips and implants, which limit the assessment of soft tissue and skeletal structures that surround the metal object.

The invention may be embodied in other specific forms without departing from the spirit or essential characteristics thereof The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

APPENDIX

Definitions
$\theta$: Projection view angle
t: Projection sample index
$P_\theta(t)$: Input rebinned projections
$I_i$: Preliminary image reconstructed from input data
$N_x$: Image size along x direction in pixels
$N_y$: Image size along y direction in pixels
(i,j): Coordinates of an image pixel located at x=i,y=j
$\mu_i$: Mean intensity of input image
Fov: Reconstructed field of view in mm
$\delta_{px}$: Pixel size along x direction in mm
$\delta_{py}$: Pixel size along y direction in mm
$(x_o,y_o)$: Coordinates of the center of the reconstructed field of view in mm
ROI ; Region of interest
$(i_c^{roi}, j_c^{roi})$: Coordinates of the center of the ROI in pixels
$(x_c^{roi}, y_c^{roi})$: Coordinates of the center of the ROI in mm
$t_c$: Projection sample that corresponds to the center of the ROI
a: Semi-major axis of ellipse inscribed within the ROI, in pixels
b: Semi-major axis of ellipse inscribed within the ROI, in pixels
$a_x$: Semi-major axis of ellipse inscribed within the ROI, in mm
$b_x$: Semi-major axis of ellipse inscribed within the ROI, in mm
$I_s$: Image containing sheet objects detected by the CFAR algorithm
$I_{shc}$: Image containing sheet objects and high contrast objects
$R_\theta(t)$: Reprojections of Image $I_{shc}$
$Q_\theta(t)$: Input projections minus reprojections
$B_\theta(t)$: Baseline values
$M_\theta(t)$: Metal projections
$I_c$: Corrected image
$I_{cm}$: Corrected image with metal pixels superimposed

EQUATIONS $$I_{shc}(i, j) = \begin{cases} I_s(i, j) & \text{if } I_s(i, j) \neq 0 \\ I_i(i, j) & \text{if } I_i(i, j) \geq \mu_i + T_{hcmax} \text{ and } (i, j) \notin metalROI \\ I_i(i, j) & \text{if } I_i(i, j) \leq \mu_i - T_{hcmin} \text{ and } (i, j) \notin metalROI \\ \mu_i & \text{otherwise} \end{cases} \qquad (1)$$

$$t\epsilon t_{ro}(\theta) \text{if} |t-t_c| \leq \sqrt{a_x^2\cos^2\theta+b_y^2\sin^2\theta}. \qquad (2)$$

$$t_s(\theta)=t_c-\lfloor\sqrt{a_x^2\cos^2\theta+b_y^2\sin^2\theta}\rfloor; \text{ and} \qquad (3)$$

$$t_e(\theta)=t_c+\lceil\sqrt{a_x^2\cos^2\theta+b_y^2\sin^2\theta}\rceil. \qquad (4)$$

$$B_\theta(t)=Q_\theta(t_s-1)+m_\theta(t_s,t_e)[Q_\theta(t)-Q_\theta(t_s-1)] \, t\epsilon t_{ro}(\theta) \qquad (5)$$

$$m_\theta(t_s, t_e) = \frac{Q_\theta(t_e+1) - Q_\theta(t_s-1)}{t_e - t_s + 2} \qquad (6)$$

$$M_\theta(t)=Q_\theta(t)-B_\theta(t), \, t\epsilon t_{ro}(\theta) \qquad (7)$$

$$I_{cm}(i, j) = \begin{cases} I_i(i, j) & \text{if } I_i(i, j) \geq T_m \text{ and } \left(\frac{i-i_c}{a}\right)^2 + \left(\frac{j-j_c}{b}\right)^2 \leq 1 \\ I_c(i, j) & \text{otherwise} \end{cases} \qquad (8)$$

$$a_x=a\delta_{px} \qquad (9)$$

$$b_y=b\delta_{py} \qquad (10)$$

$$t_c=x_c^{roi}\cos\theta+y_c^{roi}\sin\theta \qquad (11)$$

$$x_c^{roi} = i_c \delta_{px} + x_0 \quad (12)$$

$$y_c^{roi} = j_c \delta_{py} + y_0 \quad (13)$$

$$x_0 = \frac{-Fov + \delta_{px}}{2} \quad (14)$$

$$y_0 = \frac{Fov + \delta_{py}}{2} \quad (15)$$

$$\delta_{px} = \frac{Fov}{N_x} \quad (16)$$

$$\delta_{py} = \frac{Fov}{N_y} \quad (17)$$

$$\mu_i = \frac{1}{N_x N_y} \sum_{i=1}^{N_x-1} \sum_{j=1}^{N_y-1} I_i(i, j) \quad (18)$$

$$Q_\theta(t) = P_\theta(t) - R_\theta(t) \quad (19)$$

$$F_\theta(t) = P_\theta(t) - M_\theta(t) \quad (20)$$

What is claimed is:

1. A method of reducing metal artifacts in a computed tomography (CT) system comprising:
   A. generating a preliminary image from input projection data collected by the CT system;
   B. identifying metal objects in the preliminary image;
   C. generating secondary projections from said input projection data by removing projections of objects having characteristics that may cause the objects to be altered in a final artifact-corrected image;
   D. extracting the projections of metal objects identified in step B from the secondary projection data generated in step C;
   E. generating corrected projections by removing the projections of the metal objects extracted in Step D from said input projection data;
   F. generating a final image by reconstructing said corrected projections generated in step E and inserting the metal objects identified in Step B into the final image;

2. The method of claim 1 wherein Step B includes identifying objects in the preliminary image having intensities which are greater than a predetermined amount.

3. The method of claim 2 wherein Step B further includes selection of metal objects which generate artifacts.

4. The method of claim 1 wherein step C includes identifying objects in the preliminary image having characteristics which may cause the objects to be altered in a final artifact-corrected image.

5. The method of claim 4 wherein step C further includes generating a modified image by setting pixels in the preliminary image which are not included in the objects identified in step C to a calculated value.

6. The method of claim 5 wherein the calculated value is equal to mean value of the preliminary image determined using pixels other than the pixels included in the objects identified in step B.

7. The method of claim 5 wherein step C further includes reprojecting the modified image and subtracting the reprojections from the input projection data to generate secondary projections which contain the input projection data with the projections of objects identified in step C removed.

8. The method of claim 1 wherein step D includes identifying at least one region in the secondary projections which contain the projections of metal objects identified in step B.

9. The method of claim 8 wherein step D further includes determining a baseline value of each of said at least one regions.

10. The method of claim 9 wherein said baseline value of each of said at least one region is determined by linear interpolation between projection data surrounding said at least one region.

11. The method of claim 10 wherein step D further includes subtracting each baseline value from the secondary projection values in its respective region to generate projection data corresponding to said metal projections in each region.

12. The method of claim 1 wherein said objects identified in step C include objects in said preliminary image having at least one dimension which is less than a predetermined length.

13. The method of claim 12 wherein said objects identified in step C include objects in said preliminary image having an intensity which differs from the mean intensity of the preliminary image by more than a predetermined threshold.

14. The method of claim 1 wherein said objects identified in step C include objects in said preliminary image having an intensity which differs from a mean intensity of the preliminary image by more than a predetermined threshold.

15. A method of reducing metal artifacts in a computed tomography (CT) system comprising:
   A. generating a preliminary image from input projection data collected by the CT system;
   B. identifying metal objects in the preliminary image which have generated metal artifacts in the preliminary image;
   C. identifying objects in the preliminary image having characteristics which may cause the objects to be altered in a final artifact-corrected image;
   D. generating a modified image by setting pixels in the preliminary image which are not included in objects identified in step C to a mean value of the preliminary image;
   E. reprojecting the modified image;
   F. subtracting the reprojections from the input projection data to generate secondary projections containing the preliminary image with the objects identified in step C removed;
   G. identifying at least one region in the secondary image which contains projections of metal objects identified in step B;
   H. determining a baseline value of each of said at least one regions;
   I. subtracting each baseline value from the secondary projection values in its respective region to generate projection data corresponding to said metal object in each region;
   J. Subtracting said metal projection data from said input projection data to generate corrected projections;
   K. reconstructing said final artifact-corrected image by:
      a. reconstructing corrected projections; and
      b. superimposing said metal objects identified in step B into said corrected image.

16. The method of claim 4 wherein said objects identified in step C include objects in said preliminary image having at least one dimension which is less than a predetermined length.

17. The method of claim 16 wherein said objects identified in step C include objects in said preliminary image having an intensity which differs from the mean intensity of the preliminary image by more than a predetermined amount.

18. The method of claim 15 wherein said objects identified in step C include objects in said preliminary image having an intensity which differs from a mean intensity of the preliminary image by more than a predetermined amount.

19. The method of claim 15 wherein, in step G, said baseline value of each of said at least one region is determined by linear interpolation between projection values surrounding said at least one region.

20. A system for reducing metal artifacts in a computed tomography (CT) system comprising:
   a tunnel having a platform disposed therein for receiving an object to be scanned;
   an x-ray source for directing x-rays at the object to be scanned;
   a detector array including a plurality of detectors for receiving said x-rays within said tunnel; and
   processing means for reducing metal artifacts in images of the object reconstructed from the x-rays detected by said detectors, said processing means performing the steps of:
      A. generating a preliminary image from input projection data collected by the CT system;
      B. identifying metal objects in the preliminary image;
      C. generating secondary projections from said input projection data by removing projections of objects having characteristics that may cause the objects to be altered in a final artifact-corrected image;
      D. extracting the projections of metal objects identified in step B from the secondary projection data generated in step C;
      E. generating corrected projections by removing the projections of the metal objects extracted in Step D from said input projection data;
      F. generating a final image by reconstructing said corrected projections generated in step E and inserting the metal objects identified in Step B into the final image.

21. The system of claim 20 wherein Step B includes identifying objects in the preliminary image having intensities which are greater than a predetermined amount.

22. The system of claim 21 wherein Step B further includes selection of metal objects which generate artifacts.

23. The system of claim 20 wherein step C includes identifying objects in the preliminary image having characteristics which may cause the objects to be altered in a final artifact-corrected image.

24. The system of claim 23 wherein step C further includes generating a modified image by setting pixels in the preliminary image which are not included in the objects identified in step C to a calculated value.

25. The system of claim 24 wherein the calculated value is equal to mean value of the preliminary image determined using pixels other than the pixels included in the objects identified in step B.

26. The system of claim 24 wherein step C further includes reprojecting the modified image and subtracting the reprojections from the input projection data to generate secondary projections which contain the input projection data with the projections of objects identified in step C removed.

27. The system of claim 20 wherein step D includes identifying at least one region in the secondary projections which contain the projections of metal objects identified in step B.

28. The system of claim 27 wherein step D further includes determining a baseline value of each of said at least one regions.

29. The system of claim 28 wherein said baseline value of each of said at least one region is determined by linear interpolation between projection data surrounding said at least one region.

30. The system of claim 29 wherein step D further includes subtracting each baseline value from the secondary projection values in its respective region to generate projection data corresponding to said metal projections in each region.

31. The system of claim 20 wherein said objects identified in step C include objects in said preliminary image having at least one dimension which is less than a predetermined length.

32. The system of claim 31 wherein said objects identified in step C include objects in said preliminary image having an intensity which differs from the mean intensity of the preliminary image by more than a predetermined threshold.

33. The system of claim 20 wherein said objects identified in step C include objects in said preliminary image having an intensity which differs from a mean intensity of the preliminary image by more than a predetermined threshold.

* * * * *

UNITED STATES PATENT AND TRADEMARK OFFICE
CERTIFICATE OF CORRECTION

PATENT NO. : 6,721,387 B1
DATED : April 13, 2004
INVENTOR(S) : Ram Naidu et al.

It is certified that error appears in the above-identified patent and that said Letters Patent is hereby corrected as shown below:

Column 11,
Line 39, after "image", delete ";", and insert thereof -- . --;

Column 12,
Line 54, after "J.", delete "Subtracting", and insert thereof -- subtracting --.

Signed and Sealed this

Twenty-ninth Day of June, 2004

JON W. DUDAS
*Acting Director of the United States Patent and Trademark Office*